United States Patent [19]

Feier

[11] 4,161,690
[45] Jul. 17, 1979

[54] METHOD AND APPARATUS FOR PARTICLE ANALYSIS

[75] Inventor: Markus Feier, Regensdorf, Switzerland

[73] Assignee: Contraves AG, Zürich, Switzerland

[21] Appl. No.: 912,927

[22] Filed: Jun. 5, 1978

[30] Foreign Application Priority Data

Jun. 27, 1977 [CH] Switzerland .................... 7842/77

[51] Int. Cl.$^2$ ............................................. G01N 27/00
[52] U.S. Cl. ................................................ 324/71 CP
[58] Field of Search ................... 324/71 CP; 364/555; 235/92 PC; 204/1 T, 195 R

[56] References Cited

U.S. PATENT DOCUMENTS

| | | | |
|---|---|---|---|
| 2,996,917 | 8/1961 | Christoph | 73/355 |
| 3,801,901 | 4/1974 | Hogg | 324/71 CP |
| 3,821,644 | 6/1974 | Gohde et al. | 324/71 CP |
| 3,852,666 | 12/1974 | Gähwiler | 324/71 CP |
| 3,973,194 | 8/1976 | McMorris et al. | 324/71 CP |

*Primary Examiner*—G. L. Kaplan
*Attorney, Agent, or Firm*—Werner W. Kleeman

[57] ABSTRACT

A method of, and apparatus for analyzing particles suspended in a liquid, especially blood cells wherein two vessels or receivers for the liquid containing the suspended particles therein are separated by an electrically insulating wall and an elongate channel penetrates through such wall. Two supply electrodes each respectively connected with one terminal of an electrical power supply contact the liquid in a respective one of the vessels. There is provided at least one auxiliary electrode contacting the liquid in the channel, and the dimensions of each such auxiliary electrode, in a direction parallel to the lengthwise direction of the channel, is small in relation to the length of the channel. There also are provided a number of feeler or sensor means, a respective one of which is operatively associated with a respective pair of the electrodes for detecting the changes, as a function of time, of the potential difference between these electrodes. There is formed an auxiliary value correlated to the timewise course of the potential difference between a given one of the auxiliary electrodes and one of the other electrodes and there is formed a measuring value correlated to the time-wise course of the potential difference between two of the other electrodes. There is triggered sampling of the measuring value for obtaining a sampling value as a function of auxiliary value and corresponding to a particle.

12 Claims, 3 Drawing Figures

METHOD AND APPARATUS FOR PARTICLE ANALYSIS

BACKGROUND OF THE INVENTION

The present invention relates to a new and improved method of, and apparatus for, analyzing particles suspended in a liquid, especially blood cells.

The apparatus of the present invention and useful for the practice of the method aspects thereof is generally of the type comprising two vessels or containers for the suspension and separated by an insulating wall. An elongate channel piercingly extends through such insulating wall. Further, there are connected two supply electrodes each of which is in contact with the liquid in a respective one of the vessels and each such supply electrode being respectively connected to one terminal of an electrical power supply. There is also provided at least one auxiliary electrode which contacts the liquid in the channel, the dimensions of such auxiliary electrode in a direction essentially parallel to the lengthwise direction of the channel being small in relation to the length of the channel. In other words, if the conducting material of the auxiliary electrode would be replaced by an insulating material there would not occur any appreciable change of the current and potential distribution within the channel. There also are provided feeler means, wherein a respective one of such feeler means is operatively associated with a respective one of a pair of electrodes for detecting timewise changes of the potential difference between these electrodes.

Now there is already known to the art apparatus wherein there are detected changes of the potential difference between both supply electrodes and such is evaluated for particle analysis. However, disturbances arise which are predicated upon the turbulence of the liquid and the boundary or fringe effects of the electrical measuring fields. One phenomena which should be mentioned as especially disturbing is that turbulence exists in the vessel which is located at the outlet of the channel in the throughflow direction, this turbulence recycling particles which have already been measured back into the region of the measuring field. Particles which have been recirculated in this manner retrigger a change in the measured potential difference, thus falsifying the measurement result. It has already been proposed to provide a spatial limiting of the suspension in the channel. However, the equipment suitable for exploiting this technique is extremely complicated and correspondingly expensive.

There is also known to the art another type of apparatus wherein, apart from there being provided both supply electrodes, there are additionally employed two auxiliary electrodes between which there are detected changes in the potential difference and evaluated for particle analysis. Through the provision of a suitable arrangement of the auxiliary electrodes the measurement of a particle occurs at that point in time where such is dispositioned at the region of the center of the channel, i.e., at a location where disturbances in the measurement caused by turbulence and boundary phenomena of the measuring field have the least effect. What is however disadvantageous with this state-of-the-art equipment is that the reproducibility of the measurement is dependent upon the constancy of the geometric and electrochemical properties of the auxiliary electrodes. Furthermore, during cleaning of the channel there is required the greatest care in order to prevent any alteration whatsoever of the auxiliary electrodes. The operation of the apparatus is therefore correspondingly complicated, as is also the fabrication of a channel equipped with two identical auxiliary electrodes.

SUMMARY OF THE INVENTION

Hence, with the foregoing in mind it is a primary object of the present invention to provide a method of, and apparatus for, particle analysis which is not associated with the aforementioned drawbacks and limitations of the prior art proposals discussed above.

Another and more specific object of the present invention aims at the provision of a new and improved method and apparatus by means of which there are eliminated disturbances in the particle analysis caused by recirculated particles and the reproducibility of the measurement is independent of the constancy of the geometric and electrochemical properties of the auxiliary electrodes arranged at the channel.

A further and more specific object of the present invention is to combine the advantages of a particle analysis based upon evaluation of the potential difference between both supply electrodes—among other things to realize the possibility of grounding the circuit and making the measurement extensively insensitive to changes in the electrode surface because such can be extremely large—and the advantages of accomplishing a measurement at the point in time where the measured particle is located near to the center of the channel—among other things eliminating disturbances due to the boundary effects of the measuring field and due to recirculated particles—without having to tolerate the corresponding drawbacks.

Now in order to implement these and still further objects of the invention, which will become more readily apparent as the description proceeds, the inventive method of the previously mentioned type is manifested by the features that there is formed an auxiliary value which is correlated to the timewise course of the potential difference between a given auxiliary electrode and one of the other electrodes and there is also formed a measuring value which is correlated to the timewise course of the potential difference between two of the other electrodes. Further, there is triggered sampling of the measuring value for obtaining a sampling value corresponding to a particle and as a function of the auxiliary value. The sampling is preferably triggered when the auxiliary value passes through a predetermined value while maintaining a predetermined alteration or change trend, and the sampling operation is preferably triggered by an edge or flank of a pulse of the auxiliary value.

Not only is the invention concerned with the aforementioned method aspects, but as already alluded to above, relates to apparatus constructed for beneficially practicing the method. The inventive apparatus is manifested by the features that there is provided a sampling circuit for sampling the measuring value as a function of a sampling signal. There is also provided a control circuit for forming a sampling signal as a function of the auxiliary value. Preferably, the control circuit consists of a series circuit of a Schmitt-trigger having hysteresis and a monostable multivibrator or monoflop. An input of the control circuit is connected with an output of one feeler means correlated to a given one of the auxiliary electrodes. An output of the control circuit is connected to a control input of the sampling circuit and a signal input of the sampling circuit is connected to an output of another feeler means, whereas an output of the sampling circuit carries the sampling value. The sampling circuit is preferably designed as a sample and hold circuit. According to another advantageous variant construction the control circuit and the sampling or sample circuit are combined into an AND-gate circuit.

The proposed method and the proposed apparatus are preferably employed for the simultaneous analysis of particles of different size suspended in the same liquid, especially for the analysis of erythrocytes and thrombocytes in diluted blood. The function will be explained hereinafter.

When a particle passes through the channel then during successive points in time it is first located between the first supply electrode and the predetermined auxiliary electrode, then approximately at the region of the auxiliary electrode, and later between the auxiliary electrode and the second supply electrode. The measuring value is then, for instance, formed between the first and the second supply electrodes, whereas the auxiliary value is formed between the first supply electrode and the auxiliary electrode. Then the throughpassage of the particle produces a pulse of the measuring value and a pulse of the auxiliary value. The pulse of the measuring value extends over the time duration of the throughpassage of the particle along the entire length of the channel. The pulse of the auxiliary value lasts approximately throughout the time duration which the particle needs in order to pass through the channel section located in front of the auxiliary electrode, i.e., between the first supply electrode and the auxiliary electrode. The pulse of the auxiliary value thus has a descending edge when the particle passes at the auxiliary electrode, whereas at this point in time the pulse of the measuring value further has a large amplitude. However, when a particle does not pass through the channel, rather is recirculated by turbulence at the output of the channel back to the region of the measuring field, the auxiliary value remains unchanged, i.e., there is not produced any pulse of the auxiliarly value, whereas the measuring value possesses a disturbance pulse.

It should be apparent that a sampling of the measuring value triggered by a pulse of the auxiliary value only then furnishes a sampling or sample value when the particle has passed through the channel, and not then when the particle is recirculated due to turbulence. Additionally, there are locations of the channel where the boundary or fringe effect of the measuring field is not effective, i.e., when the particle is momentarily disposed at such location then the instantaneous or momentary measuring value is practically only dependent upon the particle size and practically not upon the path of travel of the particle. The sampling operation can be triggered at that point in time where the particle is disposed at such advantageous location, so that the sampling value also is not disturbed by the boundary effects of the measuring field. For this purpose the predetermined auxiliary electrode is arranged at this advantageous location of the channel or in the throughflow direction somewhat after such location, so that the pulse of the auxiliary value then terminates approximately when the particle is located at the desired location, and the sampling is triggered by the descending edge of the pulse of the auxiliary value.

In the heretofore known apparatuses for the analysis of blood samples the recirculated erythrocytes generate weak measuring signals which are approximately in the order of magnitude of the signals which normally are produced by the much smaller thrombocytes. With the proposed method and the proposed apparatus the recirculated erythrocytes do not produce any disturbance or interference signals, so that it is thus possible to count and to measure the erythrocytes and thrombocytes in the same sample. Particular, prior to counting of thrombocytes there is no longer required any pre-treatment of the sample for lysis of the erythrocytes, so that the sample preparation can be accomplished more quickly, simpler and less expensively while there is eliminated a corresponding source of error, and additionally, there is obtained a cleaner count and measurement of the particles owing to the measuring value sampling.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
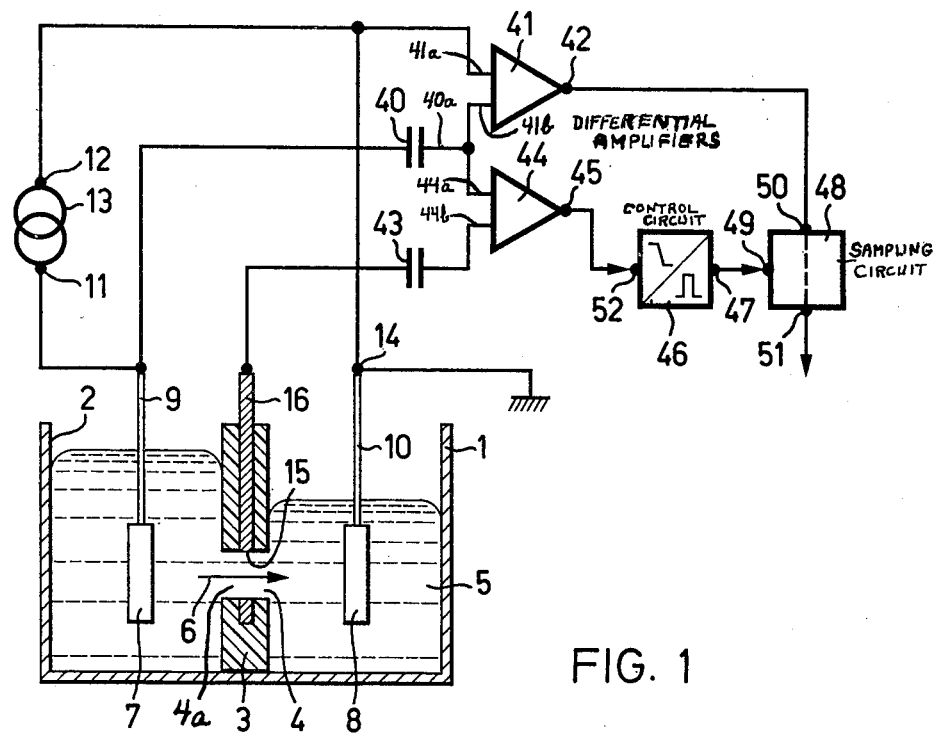
FIG. 1 schematically illustrates an exemplary embodiment of apparatus for particle analysis and useful for the practice of the method aspects.

Describing now the drawings, in FIG. 1 there are illustrated two vessels or containers 1 and 2 which are separated from one another by an electrically insulating wall 3. A channel or duct 4 piercingly penetrates through the wall 3 from one of the vessels 1 to the other vessel 2. Both vessels 1 and 2 as well as the channel 4 are filled with a suspension of particles to be analysed which are contained in a liquid 5. At the channel 4 the hydrostatic pressure of the liquid 5 in the vessel 2 is greater than in the vessel 1, so that the suspension flows in the direction of the arrow 6 through the channel 4. The hydrostatic pressure difference is obtained in conventional manner and has only therefore been symbolized in FIG. 1 in that the liquid level in the vessel 2 is higher than in the vessel 1.

In each of the vessels 1 and 2 there is arranged a respective associated supply electrode 8 and 7 which contacts the the liquid 5. The corresponding current infeed lines 9 and 10 are connected with a respective terminal 11 and 12 of a suitable electrical power supply 13. The power supply 13 delivers a constant current by appropriate lines or conductors which have not been particulary referenced. It can be advantageous to ground one of the terminals 11 or 12, for instance by means of the line junction or node 14. The metal used for forming the electrodes 7 and 8 can be any of the standard metals used in such applications, such as for instance platinum or gold.

The channel 4 shown in FIG. 1 has a substantially circular opening 4a, whose diameter for the purpose of analysing the erythrocytes (red blood cells) typically is in the order of magnitude of about 70$\mu$. An auxiliary electrode 15 is arranged at the channel 4 and is structured such that its dimension in the direction of the arrow 6 is appreciably smaller than the length of the channel 4. This auxiliary electrode 15 contacts the liquid 5 at the region of the center of the channel 4. A current infeed line or conductor 16 leading to the auxiliary electrode 15 is embedded in the insulating wall 3. Here also the electrode metal of the auxiliary electrode 15 is a metal which is conventionally employed in such applications, for instance platinum or gold. The current infeed line 16 can be formed of the same metal or, from a different metal, for instance copper, which then is coated at the region where it contacts the liquid 5 with the electrode metal, for instance can be galvanically gold plated. The wall 3 with the embedded current infeed line 16 and the auxiliary electrode 15 can be formed of three layers having a metal plate adhesively bonded between two electrically insulating plates. The channel 4 is then fabricated by drilling a hole perpendicular to the plates. The auxiliary electrode 15 consists of the gold plated surface of the copper layer which is cut by the bore 4a of the channel 4 as best seen by referring to FIG. 2.

Figure 2:
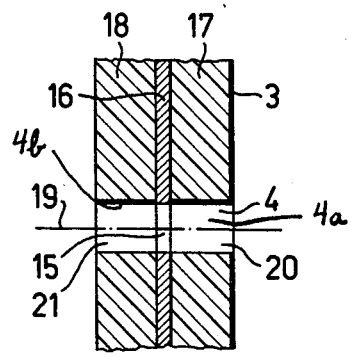
FIG. 2 is a fragmentary sectional view of the insulating wall at the region of the channel and showing a first exemplary embodiment of an auxiliary electrode.

Now in FIG. 2 there is shown in sectional view the wall 3 at the region of the channel 4. The wall 3 consists of two flat, glass fiber reinforced plastic plates 17 and 18 between which there is adhesively bonded a copper layer or copper plate 16 serving as the electrical infeed line. The channel 4 in longitudinal sectional view is in the form of a cylindrical bore 4a which is centered at the channel axis 19. The auxiliary electrode 15 is thus constructed as part of the inner wall 4b of the channel 4.

Figure 3:
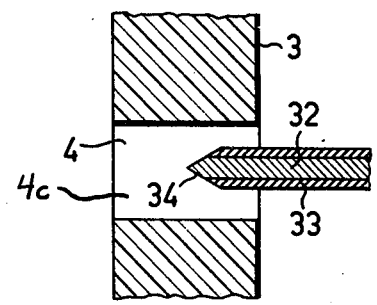
FIG. 3 is a fragementary sectional view somewhat like the showing of FIG. 2, of the insulating wall at the region of the channel and illustrating a second exemplary embodiment of an auxiliary electrode.

To the extent that the diameter of the channel 4 permits, the auxiliary electrode and its insulated electrical infeed line also could extend from one end of the channel 4 into such channel, as such has been schematically illustrated in the variant embodiment of FIG. 3. In this case the channel 4 is a simple bore or hole 4c extending through an electrically insulating wall 3. A copper rod 32 is encased by an insulating layer or coating 33 and serves as the electrical infeed line. The tip of the rod 32 is beared from the insulation, and the exposed metal part is gold plated and forms the auxiliary electrode 34. This structure, in relation to the internal dimension of the channel 4, has not been shown to scale in the drawing, rather has been illustrated with a markedly enlarged diameter, in order to improve the showing of the drawing.

The changes in the impedance of the liquid is measured between both of the supply electrodes 7 and 8. For this purpose there is conducted in conventional manner a constant current between the supply electrodes 7 and 8 through the liquid 5, so that the voltage between both supply electrodes 7 and 8 changes when a particle passes the channel 4. In standard fashion this voltage change is measured by a feeler means which essentially comprises a capacitor 40 and a differential amplifier 41. The one input 41a of the differential amplifier 41 is directly connected with the supply electrode 8 and its current infeed line 10 and the other input 41b of such differential amplifier 41 is connected by means of the capacitor 40 with the supply electrode 7 and its current infeed line 9, as shown. At an output 42 of the differential amplifier 41 there thus appears a measuring or measurement value which represents the course as a function of time of the changes of the potential difference between both of the supply electrodes 7 and 8. In similar manner there is measured the changes of the potential difference between the auxiliary electrode 15 and the supply electrode 7 by a feeler means which essentially comprises the first mentioned capacitor 40, a further capacitor 43 and a differential amplifier 44. The one input 44a of the differential amplifier 44 is connected by means of the capactor 40 with the supply electrode 7 and its current infeed line 9 and the other input 44b of this differential amplifier 44 is connected by means of the capacitor 43 with the auxiliary electrode 15 and its electrical infeed line or conductor 16. As will be apparent from the drawings, one terminal 40a of the capacitor 40 is conjointly connected with a respective input 41b and 44b of the differential amplifiers 41 and 44, respectively. At an output 45 of the differential amplifier 44 there thus appears an auxiliary value which is representative of the course as a function of time of the changes in the potential difference between the supply electrode 7 and the auxiliary electrode 15. Now if a particle passes through the channel 4 in the direction of the arrow 6, then the auxiliary value appearing at the output 45 changes. After the particle has floated past the auxiliary electrode 15, then, the auxiliary value likewise has returned back to its starting value. The gain of the differential amplifier 44 as well as the quiescent value at the output 45, corresponding to the one input value "null", can be almost randomly set in conventional manner. The same also is true for the differential amplifier 41, wherein in this case the quiescent value is advantageously null.

The operation is accomplished such that a sampling of the measuring value is carried out when the change of the auxiliary value exhibits a descending pulse edge or flank, since this approximately corresponds to the point in time where the particle floats or moves past the auxiliary electrode 15 or 34, as the case may be. There is provided a control circuit 46 whose input 52 is connected with the output 45 of the differential amplifier 44 and which delivers a control signal in response to a descending pulse edge of the auxiliary value for a predetermined value or magnitude of the auxiliary value. The control circuit 46 can be conventionally constituted, for instance, by a series circuit of a Schmitt-trigger having hysteresis and a monostable multivibrator or monoflop. The Schmitt-trigger flops over when the auxiliary value has reached a certain value after the Schmidt-trigger has been set by a higher value of the auxiliary value. The flop over of the Schmitt-trigger triggers a pulse from the monostable multivibrator or monoflop which forms the control signal and appears at an output 47 of the control circuit 46. There is also provided a sampling circuit 48 whose control input 49 is connected with the output 47 of the control circuit 46, whereas its signal input 50 is connected with the output 42 of the differential amplifier 41. This sampling circuit 48 is of known construction and functions such that there appears as the sampling value at its output 51 the same signal as at its signal input 50 as long as a pulse appears at its control input 49. According to a preferred variant the sampling or sample circuit 48 is combined in conventional manner with a hold circuit which stores the sample or sampling value at the output 51 until it is replaced by a new sampling value. The relevant last sampling value therefore is available at the output 51 until the next sampling in order to be further processed. In the embodiment under discussion each sampling value corresponds to the size of a particle passing through the channel 4, and the further processing of the sample or sampling value is accomplished in a manner conventional in a particle analyser, for instance counting and clasification according to size.

The quiescent value of the differential amplifier can be set to null. Then the value where the Schmitt-trigger flops over can be set to be somewhat greater than null. Also there can be used a different combination of quiescent value and flop-over value. What is only important is that the Schmitt-trigger flops-over in response to a descending edge or flank of the auxiliary value. In particular, the gain of the differential amplifier 44 can be extremely high, so that there appears at its output 45 either the value null or an auxiliary value which practically corresponds to the saturation state of the differential amplifier 44. The auxiliary value is then practically a logical signal having two states, and the Schmitt-trigger then need only respond to the change of the auxiliary value from the saturation value to the null value.

If the purpose of the examination or analysis resides in counting the particles—wherein recirculated particles should not be counted—then also the other differential amplifier 41 can be set to have an extremely high gain, so that at the output 42 there practically appears a logical signal. In this variant construction the control circuit 46 and the sampling circuit 48 can be replaced by a sample AND-gate circuit, at the output 51 of which there appears a logic signal when there appears in coincidence a respective logic signal at both of its inputs 50 and 52. Hence, with this modified arrangement the elements 46 and 50 can be conceptually considered to constitute such an AND-gate. The sampling signal is thus formed internally of the AND-gate circuit and evaluated. The hold circuit is then superfluous and can be dispensed with.

It will be apparent that the auxiliary electrode serves the purpose of detecting the position of the particle in the channel 4 and not for forming the measuring value. For this reason the measurement is not influenced by geometric or electrochemical changes in the auxiliary electrode. During cleaning of the channel 4 there are not needed any special precautionary measures. There can be arranged at the channel further auxiliary electrodes for other purposes, for instance for improving the measurement according to the teaching of Swiss Pat. No. 552,211, or also for screening against stray fields. Also the auxiliary value can be formed between a predestined auxiliary electrode and another auxiliary electrode.

While there are shown and described present preferred embodiments of the invention, it is to be distinctly understood that the invention is not limited thereto, but may be otherwise variously embodied and practiced within the scope of the following claims.

Accordingly, What I claim is:

1. In a method of analyzing particles suspended in a liquid by means of two vessels for the liquid containing the therein suspended particles and which vessels are separated from one another by an electrically insulating wall which has a throughpassing elongate channel, two supply electrodes each of which contacts the liquid in a respective one of the vessels and each supply electrode being connected with a terminal of an electrical power supply, at least one auxiliary electrode contacting the liquid in the channel, the dimension of the auxiliary electrode in a direction essentially parallel to the lengthwise direction of the channel being small in relation to the length of the channel, and at least two feeler means, one of which is operatively associated with a pair of electrodes for determining the timewise course of the potential difference between such electrodes, the improvement which comprises:

forming an auxiliary value correlated to the timewise course of the potential difference between a predetermined auxiliary electrode and one of the other electrodes;

forming a measuring value correlated to the timewise course of the potential difference between two of the other electrodes; and sampling the measuring value for obtaining a sampling value corresponding to a particle and as a function of the auxiliary value.

2. The method as defined in claim 1, comprising the steps of:

employing said method for analyzing particles of different size suspended in the same liquid.

3. The method as defined in claim 2, wherein:

the liquid is diluted blood and the particles of different size which are analyzed are erythrocytes and thrombocytes.

4. The method as defined in claim 1, further including the steps of:

triggering the sampling operation when the auxiliary value has passed through a predetermined value while maintaining a predetermined trend change.

5. The method as defined in claim 4, further including the steps of:

triggering the sampling by means of an edge of a pulse of the auxiliary value.

6. The method as defined in claim 1, further including the steps of:

employing a sampling circuit for sampling the measuring value as a function of a sampling signal; and employing a control circuit for forming the sampling signal as a function of the auxiliary value.

7. In a method of analyzing particles suspended in a liquid by means of two vessels for the liquid containing the therein suspended particles and which vessels are separated from one another by a wall having a throughflow channel, two supply electrodes each of which contacts the liquid in a respective one of the vessels and each supply electrode being connected with a terminal of an electrical power supply, at least one auxiliary electrode contacting the liquid in the channel, and at least two feeler means, one of which is operatively associated with a pair of electrodes for determining the timewise course of the potential difference between such electrodes, the improvement which comprises:

forming an auxiliary value correlated to the timewise course of the potential difference between the auxiliary electrode and one other electrode;

forming a measuring value correlated to the timewise course of the potential difference between said two supply electrodes; and sampling the measuring value for obtaining a sampling value corresponding to a particle and as a function of the auxiliary value.

8. The method as defined in claim 7, including the steps of:

using as said one other electrode one electrode of said two supply electrodes.

9. An apparatus for analyzing particles suspended in a liquid, especially blood cells, comprising:

a pair of vessels for the liquid containing the particles suspended therein;

an electrically insulating wall separating the vessels from one another;

said wall having an elongate channel means piercingly extending therethrough for flow communicating said pair of vessels with one another;

an electrical power supply having a pair of terminals;

a respective supply electrode arranged in each of the vessels and contacting the liquid contained therein;

each supply electrode being operatively connected with a respective terminal of the electrical power supply;

at least one auxiliary electrode contacting the liquid in the channel means;

said auxiliary electrode having a dimension extending essentially parallel to the lengthwise direction of the channel which is small in relation to the length of the channel means;

at least two feeler means having input means and output means;

each of said feeler means being operatively connected to a respective pair of said electrodes for detecting the changes as a function of time of the potential difference between such electrodes;

an auxiliary value being formed by the timewise course of the potential difference between said auxiliary electrode and one of the supply electrodes;

a measuring value being formed by the timewise course of the potential difference between the two supply electrodes;

a sampling circuit for sampling the measuring value as a function of a sampling signal for forming a sampling value;

a control circuit having an input and output for forming the sampling signal as a function of the auxiliary value;

said control circuit comprising a series circuit of a Schmitt-trigger having hysteresis and a monostable multivibrator;

said control circuit having an input connected with the output means of one of said feeler means operatively associated with the auxiliary electrode;

said sampling circuit having a control input and a signal input and an output;

said output of the control circuit being connected with the control input of the sampling circuit;

said signal input of the sampling circuit being connected with the output means of the other feeler means; and the sampling value appearing at the output of the sampling circuit.

10. The apparatus as defined in claim 9, wherein:
said sampling circuit constitutes a sample-and-hold circuit.

11. The apparatus as defined in claim 9, wherein:
said sampling circuit and said control circuit constitute an AND-gate circuit.

12. An apparatus for analyzing particles suspended in a liquid, especially blood cells, comprising:

two receiver means for the liquid containing the particles suspended therein;

a wall separating the two receiver means from one another;

said wall having a throughflow channel for flow communicating said two receiver means with one another;

an electrical power supply having a pair of terminals;

a respective supply electrode arranged in each of the receiver means and contacting the liquid contained therein;

each supply electrode being operatively connected with a respective terminal of the electrical power supply;

at least one auxiliary electrode contacting the liquid in the channel means;

at least two feeler means having input means and output means;

each of said feeler means being operatively connected with a respective pair of electrodes for detecting the changes as a function of time of the potential difference between such electrodes;

an auxiliary value being formed by the timewise course of the potential difference between said auxiliary electrode and one other electrode;

a measuring value being formed by the timewise course of the potential difference between the two supply electrodes;

a sampling circuit for sampling the measuring value as a function of a sampling signal for forming a sampling value;

a control circuit having an input and output for forming the sampling signal as a function of the auxiliary value;

said control circuit having an input connected with the output means of one of said feeler means operatively associated with the auxiliary electrode;

said sampling circuit having a control input and a signal input and an output;

said output of the control circuit being connected with the control input of the sampling circuit;

said signal input of the sampling circuit being connected with the output means of the other feeler means; and the sampling value appearing at the output of the sampling circuit.

* * * * *